United States Patent [19]
Peifer et al.

[11] Patent Number: 5,987,519
[45] Date of Patent: Nov. 16, 1999

[54] TELEMEDICINE SYSTEM USING VOICE VIDEO AND DATA ENCAPSULATION AND DE-ENCAPSULATION FOR COMMUNICATING MEDICAL INFORMATION BETWEEN CENTRAL MONITORING STATIONS AND REMOTE PATIENT MONITORING STATIONS

[75] Inventors: John W. Peifer; Andrew Hopper, both of Atlanta; Michael Burrow; Barry Sudduth, both of Lawrenceville; Samir Panchal, Norcross; Andy Quay, Kennesaw; W. Edward Price, Smyrna, all of Ga.; John R. Searle, Houston, Tex.

[73] Assignee: Georgia Tech Research Corporation, Atlanta, Ga.

[21] Appl. No.: 08/933,388

[22] Filed: Sep. 19, 1997

Related U.S. Application Data

[60] Provisional application No. 60/026,986, Sep. 20, 1996.

[51] Int. Cl.[6] .................................................. G06F 13/00
[52] U.S. Cl. ........................ 709/230; 709/240; 709/205
[58] Field of Search ..................................... 600/595, 509, 600/300; 709/246, 230, 240, 205

[56] References Cited

U.S. PATENT DOCUMENTS

| | | | |
|---|---|---|---|
| 4,259,548 | 3/1981 | Fahey et al. | 179/5 R |
| 4,838,275 | 6/1989 | Lee | 128/670 |
| 5,339,821 | 8/1994 | Fujimoto | 128/700 |
| 5,434,611 | 7/1995 | Tamura | 348/8 |
| 5,438,607 | 8/1995 | Przygoda, Jr. et al. | 379/38 |
| 5,441,047 | 8/1995 | David et al. | 128/670 |
| 5,488,412 | 1/1996 | Majeti et al. | 348/10 |
| 5,502,726 | 3/1996 | Fischer | 370/94.1 |
| 5,544,649 | 8/1996 | David et al. | 128/630 |
| 5,553,609 | 9/1996 | Chen et al. | 128/630 |
| 5,558,638 | 9/1996 | Evers et al. | 604/66 |
| 5,576,952 | 11/1996 | Stutman et al. | 364/413.02 |
| 5,619,991 | 4/1997 | Sloane | 600/300 |
| 5,640,953 | 6/1997 | Bishop et al. | 128/630 |
| 5,666,487 | 9/1997 | Goodman et al. | 709/246 |
| 5,687,734 | 11/1997 | Dempsey et al. | 600/509 |
| 5,810,747 | 8/1998 | Brundy et al. | 600/595 |

*Primary Examiner*—Le Hien Luu
*Attorney, Agent, or Firm*—Thomas, Kayden, Horstemeyer & Risley, L.L.P.

[57] ABSTRACT

The present invention provides a packet-based telemedicine system for communicating video, voice and medical data between a central monitoring station and a patient monitoring station which is remotely-located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combinations of network architectures, including a Community access Television (CATV) network, the Public Switched Telephone Network (PSTN), the Integrated Services Digital Network (ISDN), the Internet, a local area network (LAN), a wide are network (WAN), over a wireless communications network, or over an asynchronous transfer mode (ATM) network. Thus, a separate transmission protocol is not required for each different type of transmission media. Rather, a single transport/network layer protocol is used for encapsulating the information in packets at the sending end and for de-encapsulating the information at the receiving end. Furthermore, by sending the information in packets, the video, voice and measurement data can be integrated and sent over a single network.

19 Claims, 5 Drawing Sheets

TELEMEDICINE SYSTEM USING VOICE VIDEO AND DATA ENCAPSULATION AND DE-ENCAPSULATION FOR COMMUNICATING MEDICAL INFORMATION BETWEEN CENTRAL MONITORING STATIONS AND REMOTE PATIENT MONITORING STATIONS

CROSS REFERENCE TO RELATED APPLICATION

This application claims priority to and the benefit of the filing date of copending provisional application entitled AN ELECTRONIC HOUSE CALL SYSTEM, assigned Ser. No. 60/026,986, filed Sep. 20, 1996, which is hereby incorporated herein by reference.

GOVERNMENT CONTRACT

The U.S. Government has a paid-up license in this invention and the right under limited circumstances to require the patent owner to license others on reasonable terms as provided for by the terms of Contract No. DAMD17-95-2-5020 awarded by the U.S. Army Medical Research and Material Command of the U.S. Government.

TECHNICAL FIELD OF THE INVENTION

This invention generally relates to the field of telemedicine and, more particularly, to a telemedicine system which communicates information between central monitoring stations and remotely-located patient monitoring stations by encapsulating the data in packets which can be sent over multiple types or combinations of network architectures.

BACKGROUND OF THE INVENTION

Generally, telemedicine is a term used to describe a type of patient care which involves monitoring of a patient's condition by a healthcare worker located at a healthcare facility which is remote with respect to the location of the patient. Telemedicine, if adequately employed, is capable of providing enormous benefits to society. One such benefit is that patients can be examined without having to travel to a healthcare facility. This feature is particularly important for patients who live in remote areas who may not be able to easily travel to the nearest healthcare facility, or who need to be examined by a healthcare worker located far away from the patient, in another state, for example.

Another benefit of telemedicine is that it is capable of allowing a patient to be examined more often than would be possible if the patient were required to travel to a healthcare facility due to the ease with which it can be administered. For example, if a patient's condition requires that measurements be taken several times a day, it would be impractical for the patient to travel to and from a healthcare facility each time a measurement needs to be taken. It probably would be necessary for the patient to be admitted to the healthcare facility. The use of telemedicine could allow these measurements to be taken at the patient's home while the healthcare worker observed the patient or the measurement data from the healthcare facility.

Another benefit of telemedicine is that it allows a patient to be examined in a more timely manner than if the patient was required to travel to the healthcare facility. This is important in urgent situations, such as when a patient's condition becomes critical and emergency procedures must be taken immediately.

Many various types of telemedicine systems are known. One example of such a system is disclosed in David et al., U.S. Pat. No. 5,441,047, issued Aug. 15, 1995, which discloses an ambulatory patient health monitoring system for monitoring a remotely-located healthcare patient from a central station. The system includes instruments at the remote location for measuring the medical condition of the patient. The medical condition may correspond to health parameters, such as heart rate, respiratory rate, pulse oximetry and blood pressure. The system includes a first audio-visual camera disposed at the patient location and a second audio-visual camera disposed at the central station. Audio and video information is transmitted between the patient's remote location and the central station via a communications network, such as an interactive cable television network. Patient data is transmitted between the patient remote location and the central station by a separate communications network, such as satellite, radio transmission or telephone lines. A display is located at the patient's remote location and at the central station to allow the patient and the healthcare worker to observe each other simultaneously.

One of the disadvantages of the system disclosed in the David et al. patent is that, although it refers to sending the information between the healthcare worker and the patient via various types of networks, the information sent from the patient's home will have to be formatted in accordance with a different communications protocol for each of these different networks. Therefore, although the David et al. patent refers to the capability of using different types of networks, the system disclosed in the David et al. patent is not "network-independent" because the data must be formatted in accordance with a particular protocol at the sending end and the formatting process will have to be reversed at the receiving end in a different manner for each type of network. At the very least, this will require different software and/or hardware at each end for each different transmission media used. Another disadvantage of the system disclosed in the David et al. patent is that the audio and video data are sent over one communications network and the patient data is sent over another communications network.

Another example of a telemedicine system is disclosed in Tamura, U.S. Pat. No. 5,434,611, issued Jul. 18, 1995. This patent discloses a telemedicine system having a two-way CATV network for transmitting images, voice and data between equipment located at the patient's home and equipment located at a medical office. Cameras are located in both the patient's home and in the medical office to provide return images between the doctor and the patient. In order for the doctor's terminal to communicate with the patient's terminal, the doctor's terminal sends a signal over a control line to the patient's terminal. A line controller then selects a communication channel for the session by selecting an unused channel in a multiple channel access (MCA) system. The terminals then automatically tune to the assigned communications channel and the information is communicated over the assigned channel between the patient and the doctor.

One disadvantage of the system disclosed in the Tamura patent is that any communication between the doctor and patient must be set up by sending a signal which the line controller detects. The line controller then selects an unused channel for the communication. It also appears that the signal must be initiated by the doctor because the text of the patent only describes the situation where the doctor sends the signal to initiate the session. In any event, the system requires that a direct connection be made between the patient's terminal and the doctor's terminal. No provision is made for allowing medical measurement data to be sent to the doctor's terminal without a direct connection being made between the patient's terminal and the doctor's terminal. Therefore, in accordance with the system disclosed in the Tamura patent, it would be impossible for information relating to the patient's condition to be sent by the patient's terminal to the doctor's terminal in the absence of a direct connection being made between the terminals, which requires that the doctor be present for the session.

It would be advantageous to provide a telemedicine system which would allow either a patient or a healthcare worker to initiate a diagnostic session to cause diagnostic measurements to be taken and sent to a location, such as a healthcare facility, where medical files could be automatically updated by the data. One advantage of such a system is that a healthcare worker would not have to administer a diagnostic session and, therefore, would not have to participate in the session. Another advantage of such a system is that medical files could be automatically updated without any action on the part of a healthcare worker being required. Furthermore, as the medical files are automatically updated, the patient's condition could be automatically monitored so that, in the event that the patient's condition falls below a predetermined level, remedial measures can be taken. It would also be advantageous to provide a telemedicine system which would allow video, voice and medical data to be integrated and sent over a single network.

Accordingly, a need exists for a telemedicine system which is network-independent and which is capable of allowing video, voice and data relating to the patient's condition to be integrated and sent from a remotely-located patient terminal to a healthcare facility without the necessity of a direct connection being set up between the patient and the healthcare worker.

SUMMARY OF THE INVENTION

The present invention provides a packet-based telemedicine system for communicating video, voice and medical data between a central monitoring station and a patient monitoring station which is remotely-located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combinations of network architectures, including a Community Access Television (CATV) network, the Public Switched Telephone Network (PSTN), the Integrated Services Digital Network (ISDN), the Internet, a local area network (LAN), a wide are network (WAN), over a wireless communications network, or over an asynchronous transfer mode (ATM) network. Thus, a separate transmission protocol is not required for each different type of transmission media. Rather, a single transport layer protocol is used for encapsulating the information in packets at the sending end and for de-encapsulating the information at the receiving end. Furthermore, by sending the information in packets, the video, voice and measurement data can be integrated and sent over a single network.

When the information has been de-encapsulated at the central monitoring station, the information is processed and analyzed by software and/or hardware to determine which patient caused the information to be sent, the type of diagnostic measurement comprised in the information, and the diagnostic measurement represented by the information.

The patient monitoring station of the telemedicine system of the present invention comprises a plurality of medical devices which are connected to a control unit via a medical device interface which controls the transmission of data from the medical devices to the control unit. The patient monitoring station is configured so that the control unit and the medical devices can communicate with each other through the medical device interface. The medical device interface preferably uses a single interrupt to request data transfer to the control unit. When the control unit has data to send to one of the medical instruments, it transmits the data to the medical device interface along with the address of the medical device that is to receive the data. The medical device interface then decodes the address and transmits the data to the proper medical device.

When a medical device has data to send to the control unit, it transmits the data to the medical device interface. The medical device interface then sends an interrupt request to the control unit. The control unit processes the interrupt request and the data is transmitted from the medical device interface to the control unit. The control unit then formats the data and outputs it to a communications device, preferably a LAN card, which encapsulates the data in accordance with the transport layer protocol and outputs it onto the network to be sent to the central monitoring station.

The control unit of the patient monitoring station also comprises a videoconferencing interface device which formats voice and video data received by the videoconferencing interface device from a camera and microphone located at the patient monitoring station. The control unit then delivers the formatted video and voice data to the communications device which encapsulates the data in accordance with the communications protocol and outputs it onto the network to be sent to the central monitoring station.

The central monitoring station also comprises a control unit which preferably is identical to the control unit of the patient monitoring station. The control unit of the central monitoring station communicates with a videoconferencing interface device of the central monitoring station which formats voice and video data received by the videoconferencing interface device from a camera and microphone located at the central monitoring station. The control unit then delivers the formatted video and voice data to a communications device, preferably a LAN card, which encapsulates the video and voice data in accordance with the transport layer protocol and outputs it onto the network to be sent to the patient monitoring station.

When the control unit of the patient monitoring station receives packets of data sent to it from the central monitoring station, the communications device of the patient monitoring station de-encapsulates the packets of information and determines whether the information is to be sent via the medical device interface to one of the medical devices or whether the information is to be sent to a display screen and speaker via the videoconferencing interface device. Once this determination is made, the information is sent to the appropriate interface device.

When the control unit of the central monitoring station receives packets of data sent to it from the patient monitoring station, the communications device of the central monitoring station de-encapsulates the packets of information and determines whether the information is diagnostic data from one of the medical devices or whether the information is videoconferencing information. If the information is videoconferencing information, the information is sent to the videoconferencing interface device. The videoconferencing interface device decodes the information and outputs it to a display screen and speaker located at the central monitoring station. If the information is diagnostic data, the control unit interprets the data. Once the diagnostic data has been interpreted, the control unit may further process the data and/or save it in a storage device.

DETAILED DESCRIPTION OF THE PREFERRED EMBODIMENT

Figure 1:
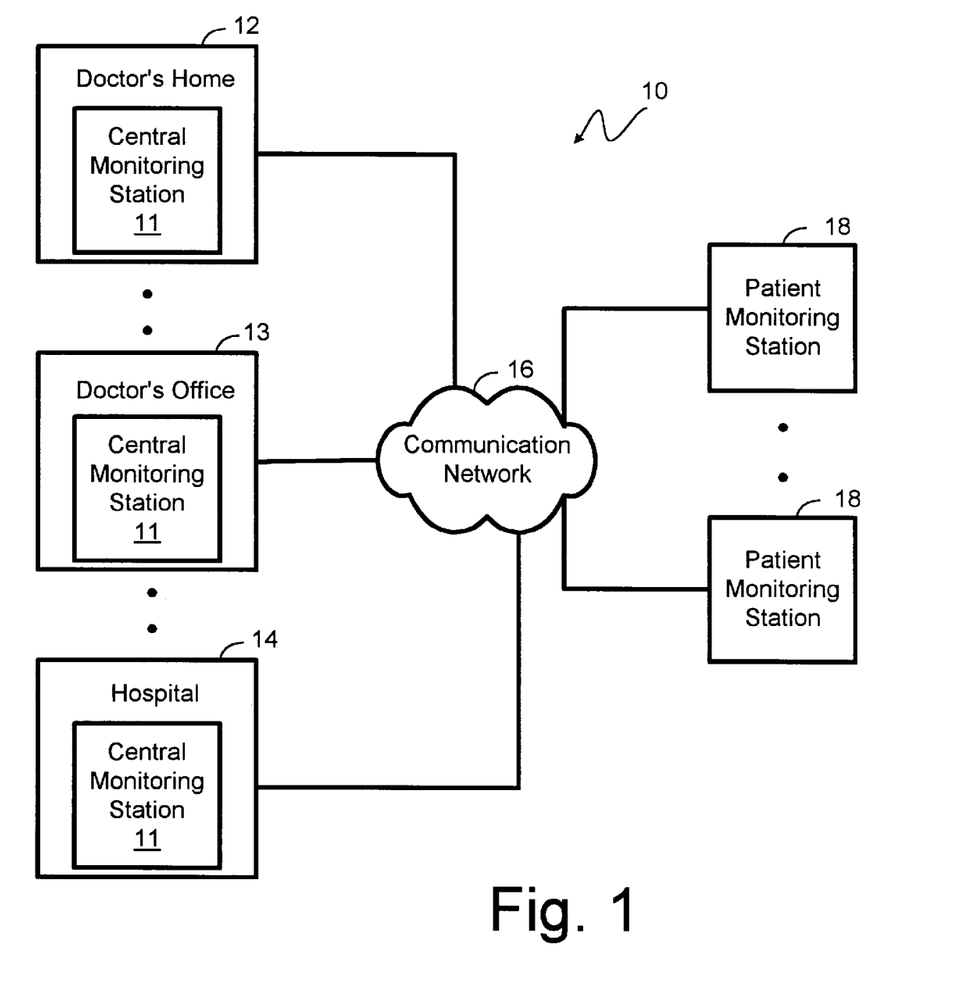
FIG. 1 is a block diagram of the telemedicine system of the present invention comprising a plurality of patient monitoring stations and a plurality of central monitoring stations.

FIG. 1 illustrates the telemedicine system 10 of the present invention comprising a plurality of central monitoring stations 11 which are in communication via a network 16 with a plurality of patient monitoring stations 18. As illustrated, a central monitoring station 11 may be provided at, for example, the doctor's home 12, the doctor's office 13, or at a hospital 14, each of which are in communication with network 16. In accordance with the present invention, data of various types is sent to and from one or more of the central monitoring stations 11 to and from one or more of the patient monitoring stations 18 in the form of digital packets, as discussed in more detail below with respect to FIGS. 2–5. It should be noted that the patient monitoring stations 18 and the central monitoring stations 11 may be located at any location capable of having access to communication network 16. It should also be noted that a plurality of patient monitoring stations 18 can communicate with a single central monitoring station 11 and that a plurality of central monitoring stations 11 can communicate with a single patient monitoring station 18.

Network 16 can be multiple types or combinations of network architectures, including the PSTN, ISDN, a cellular or wireless network, a LAN, a WAN, a Community Access Television network (CATV), the Internet, an ATM network, or a combination of one or more of these networks. All of the information transmitted between a patient monitoring station 18 and a central monitoring station 11 is encapsulated in packets using a preselected communications protocol. In accordance with the preferred embodiment of the present invention, TCP/IP is used as the transport layer/network layer protocol for encapsulating the data in packets. However, it will be apparent to those skilled in the art that other types of communications protocols are suitable for use with the present invention. TCP/IP is preferred due to its wide acceptance and use.

Figure 2:
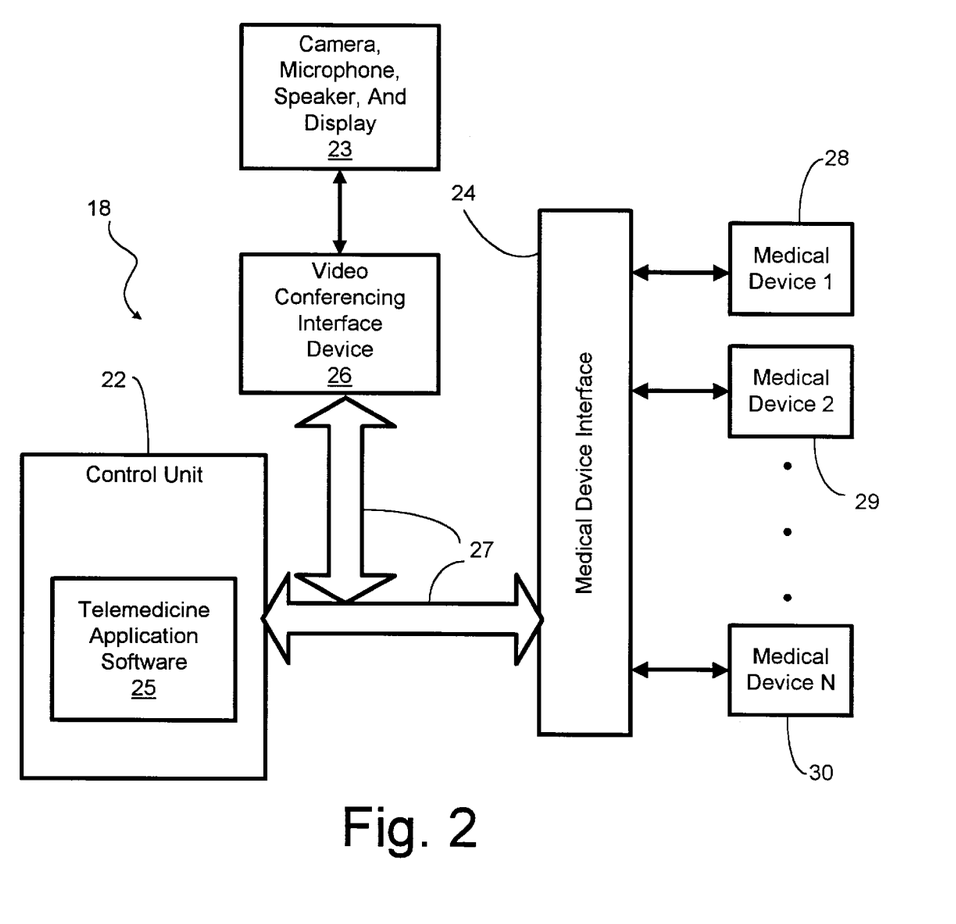
FIG. 2 is a block diagram of one of the patient monitoring stations shown in FIG. 1 comprising N medical devices connected via a device interface to a control unit.

FIG. 2 is a block diagram demonstrating one of the patient monitoring stations 18 shown in FIG. 1. Each patient monitoring station 18 comprises a control unit 22, an address/data bus 27, a videoconferencing interface device 26, videoconferencing equipment 23, a medical device interface 24, and one or more medical devices 28–30. In accordance with the preferred embodiment of the present invention, medical device interface 24 comprises a serial card that has multiple serial ports and uses only one interrupt line (not shown) to communicate with control unit 22. The medical device interface 24 is connected to a plurality of medical devices 28–30 and to the control unit 22 via address/data bus 27. The control unit 22 comprises telemedicine application software 25 which controls the flow of data to and from the medical devices 28–30 via the medical device interface 24.

Videoconferencing interface device 26 comprises hardware and/or software which controls the processing of data received by the control unit 22 from the videoconferencing equipment 23 to convert the data into a form which is suitable for transmission over network 16. The videoconferencing interface device 26 is also responsible for processing videoconferencing data received from the central monitoring station to convert the data into a form which is suitable for display on a display screen comprised by videoconferencing equipment 23.

When data is to be sent from the control unit 22 to one of the medical devices 28–30, the control unit 22 sends data to medical device interface 24 via address/data bus 27. Medical device interface 24 then transmits the data to the appropriate medical device 28–30 by decoding the address information placed on the address/data bus 27. When data is to be sent to control unit 22 from one of the medical devices, the medical device transmits the data to medical device interface 24. Medical device interface 24 then buffers and queues the requests and then uses a single interrupt line to indicate that it has data to transmit to control unit 22. Once control unit 22 is prepared to receive the data, medical device interface 24 sends the data to control unit 22 via the address/data bus 27.

The medical devices 28–30 can include, but are not limited to, blood pressure devices, thermometers, pulse oximetry devices, electrocardiograms (EKGs), scales and stethoscopes. Additionally, medical devices can be freely interchanged with one another simply by unplugging one medical device from the interface and plugging in another. This "plug and play" compatibility, is made possible by the system configuration and use of a single interrupt interface and provides maximum flexibility in configuring the telemedicine system to meet particular needs. Numerous combinations of different medical devices can be used in one telemedicine system via the device interface. The device interface itself can be implemented in numerous ways, including but not limited to, an RS-232 interface, a single serial communications card, a bus such as the Firewire (IEEE 1394) or Universal Serial Bus (USB), or any other interface which uses a single interrupt in the data transfer process. The control unit can also be implemented in numerous ways including, but not limited to, a personal computer or any other type of processing unit.

Figure 3:
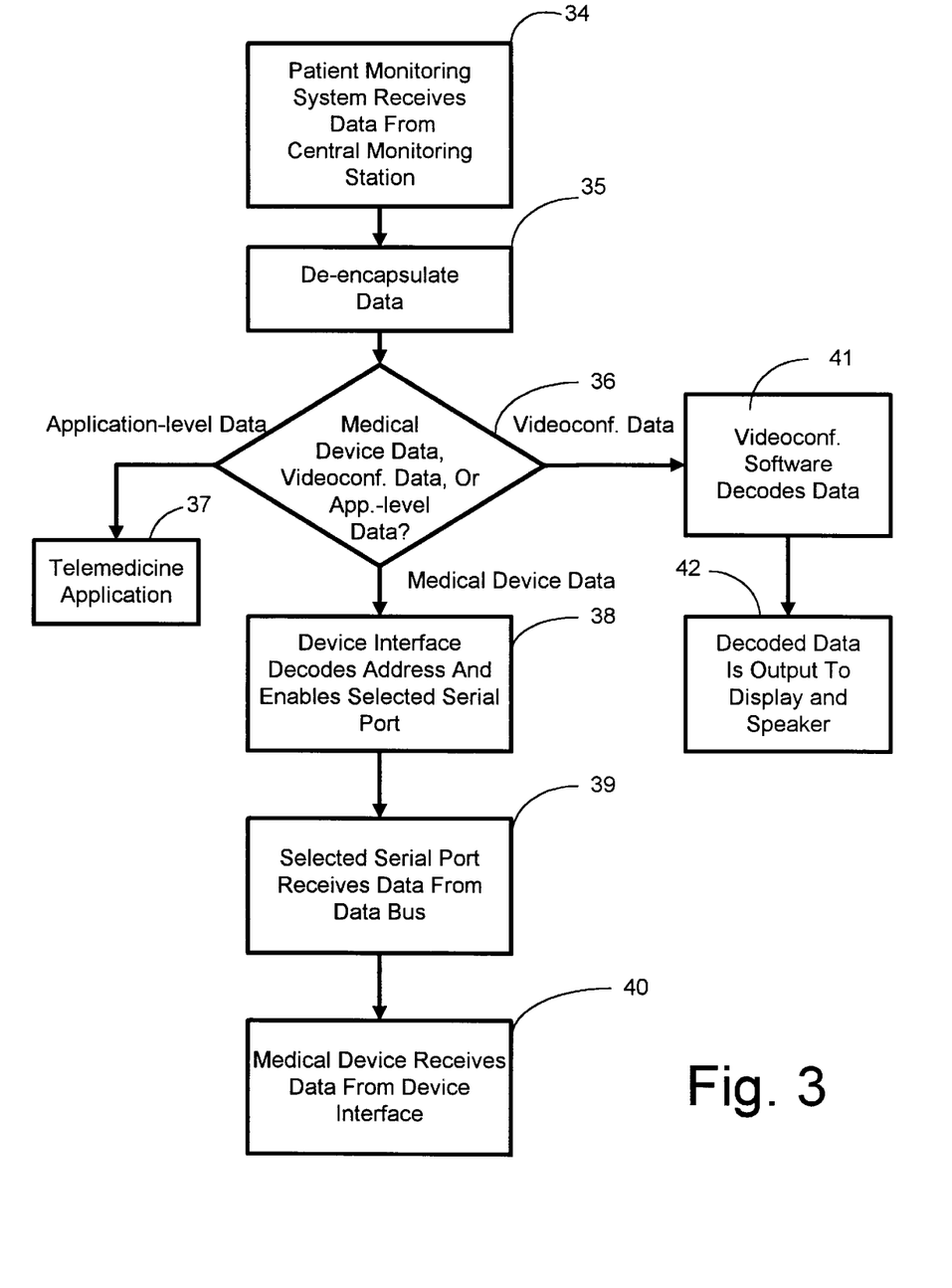
FIG. 3 is a flow chart demonstrating the processing of data received by the control unit shown in FIG. 2 from one of the central monitoring stations shown in FIG. 1.
Figure 4:
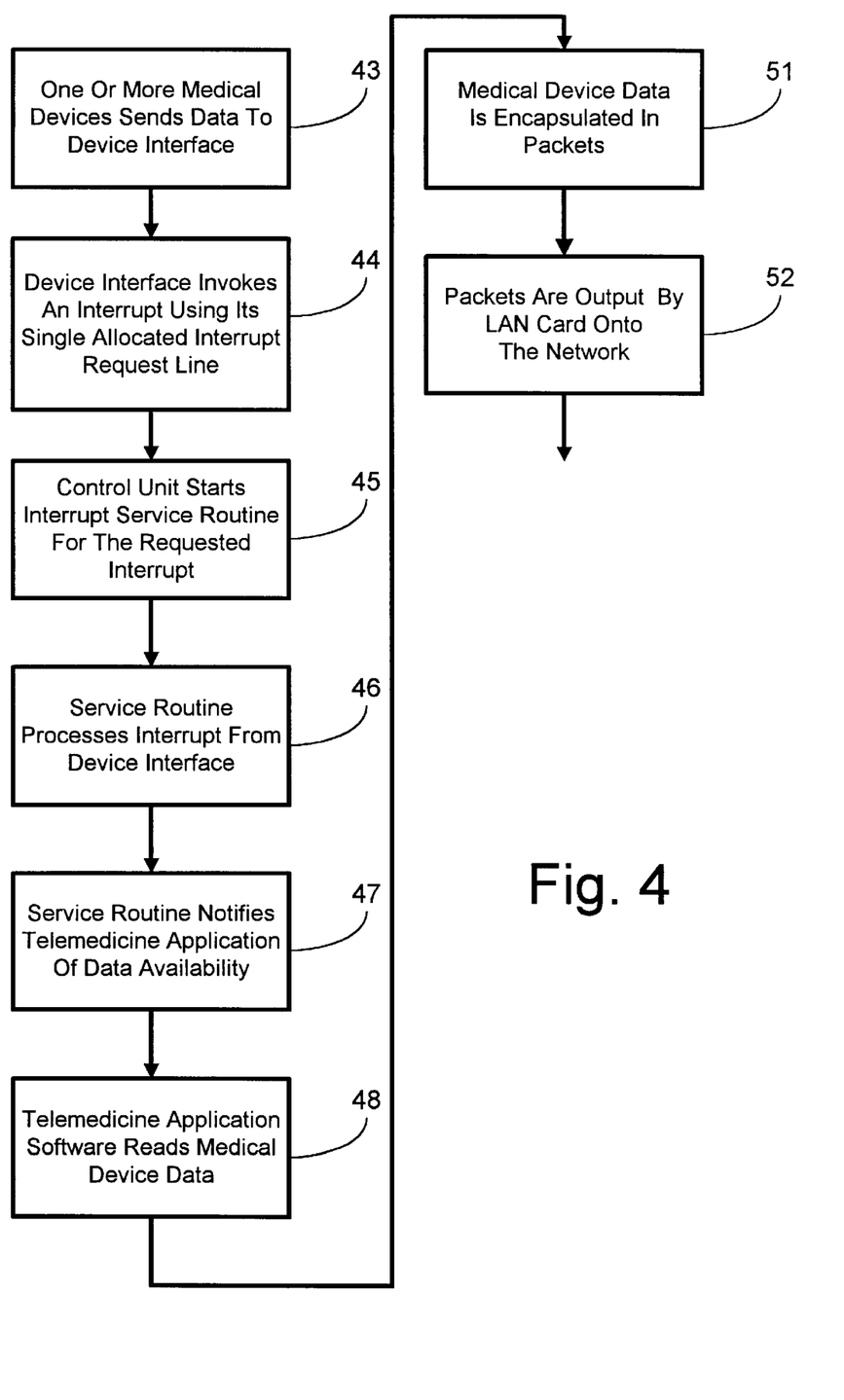
FIG. 4 is a flow chart demonstrating the transmission of data from one of the medical devices shown in FIG. 2 to the control unit shown in FIG. 2 and then to the central monitoring station shown in FIG. 1.

FIGS. 3 and 4 generally portray the steps involved in a transfer of data between a medical device and control unit 22. With respect to FIG. 3, when the patient monitoring station 18 receives data from the central monitoring station 11, control unit 22 determines whether the data is directed to one of the medical devices 28–30, to the videoconferencing equipment 23, or to application-level data, as indicated by block 34. The received information is encapsulated in packets of digital data. The communications device (not shown) of the control unit 22 de-encapsulates the packets and the data is analyzed to determine whether the data is videoconferencing data, medical instrument command data, or application-level data, as indicated by block 35 and 36, respectively. If the data is directed to the videoconferencing equipment 23, the data is processed by the videoconferencing interface device 26 and output to videoconferencing equipment 23, as indicated by blocks 41 and 42, respectively. This data can be control commands and data for controlling the operation of the videoconferencing equipment 23 (e.g., controlling the pan or tilt of the camera), or it can be image and voice data captured by the videoconferencing apparatus located at the central monitoring station 11, as discussed in more detail below.

If it is determined at block 36 that the data is application-level data, the data is processed within the control unit 22 by the telemedicine application, as indicated by block 37. Application-level data may be, for example, a message to the patient, status information, etc.

If it is determined at block 36 that the received data is medical device command data, the medical device interface 24 decodes the address and enables the selected serial port corresponding to the requested medical device, as indicated by block 38. The selected serial port receives the data from the address/data bus 27, as indicated by block 39. The intended medical device then receives the data from medical device interface 24 over the selected serial port (not shown).

FIG. 4 is a block diagram illustrating the transfer of data from one of the medical devices 28–30 to the control unit 22. In accordance with the preferred embodiment of the present invention, medical device interface 24 comprises a serial interface card with one serial port connected to each medical device 28–30. As before, the telemedicine application software 25 is running on control unit 22 during the transmission process. In step 43, one or more of the medical devices 28–30 sends data to medical device interface 24. The medical device interface 24 buffers and queues the data and then invokes an interrupt using the single interrupt line (not shown), as indicated by block 44. The control unit 22 then invokes an interrupt service routine to handle the interrupt request, as indicated by block 45. As stated above, numerous routines for processing the resulting data can be included in the telemedicine application software 25 for acquiring data from the various types of medical devices and for converting the data into a form suitable for transmission to the central monitoring station 11. It will be understood by those skilled in the art which types of routines will be needed and the manner in which those routines should be constructed to accomplish these tasks.

Once the interrupt service routine has been invoked, it processes the interrupt and notifies the telemedicine application software 25 of the availability of the data, as indicated by blocks 46 and 47. The telemedicine application software 25 then reads the data sent by the medical device, as indicated by block 48. The medical device data is then sent by the control unit 22 to the communications device, which preferably is a LAN card (not shown), which encapsulates the data in packets, as indicated by block 51. The packets are then output by the LAN card onto the network 16, as indicated by block 52.

The medical device interface 24 can include numerous serial ports to handle data sent by multiple medical devices 28–30. In essence, medical device interface 24 itself handles all data transfer, buffering, and priority functions associated with using a single interrupt. Therefore, since numerous combinations of medical devices 28–30 can be connected to device interface 24, device interface 24 in conjunction with the telemedicine application software 25 provides a "plug-and-play" type of compatibility between the control unit 22 and the medical devices 28–30. Therefore, medical devices 28–30 can be connected and disconnected from device interface 24 in any combination. This feature of the single interrupt interface 24 and telemedicine application software 25 provides maximum flexibility in configuring the telemedicine system 10.

Additionally, the telemedicine application software 25 in conjunction with the interface 24 may perform any necessary conversion functions. The telemedicine application software 25 can include routines for converting data into a form comprehensible by one or more medical devices 28–30, by the control unit 22, or by medical device interface 24. This interpretation function facilitates communication among different devices and allows the effective use of the single interrupt device interface 24. However, it should be noted that although the single interrupt architecture of the present invention is preferred, it will be apparent to those skilled in the art that this is not necessary and that any means by which one or more medical devices 28–30 can transfer data to and from the medical devices 28–30 to and from the control unit 22 is suitable for use with the present invention.

The telemedicine application software 25 in conjunction with medical device interface 24 may also perform the function of allowing medical devices using different protocols to communicate. For example, the protocol used by a medical device 28–30 may be different from any other medical device. The telemedicine application software 25 can contain routines for allowing these different protocols to communicate via the common device interface 24.

Figure 5:
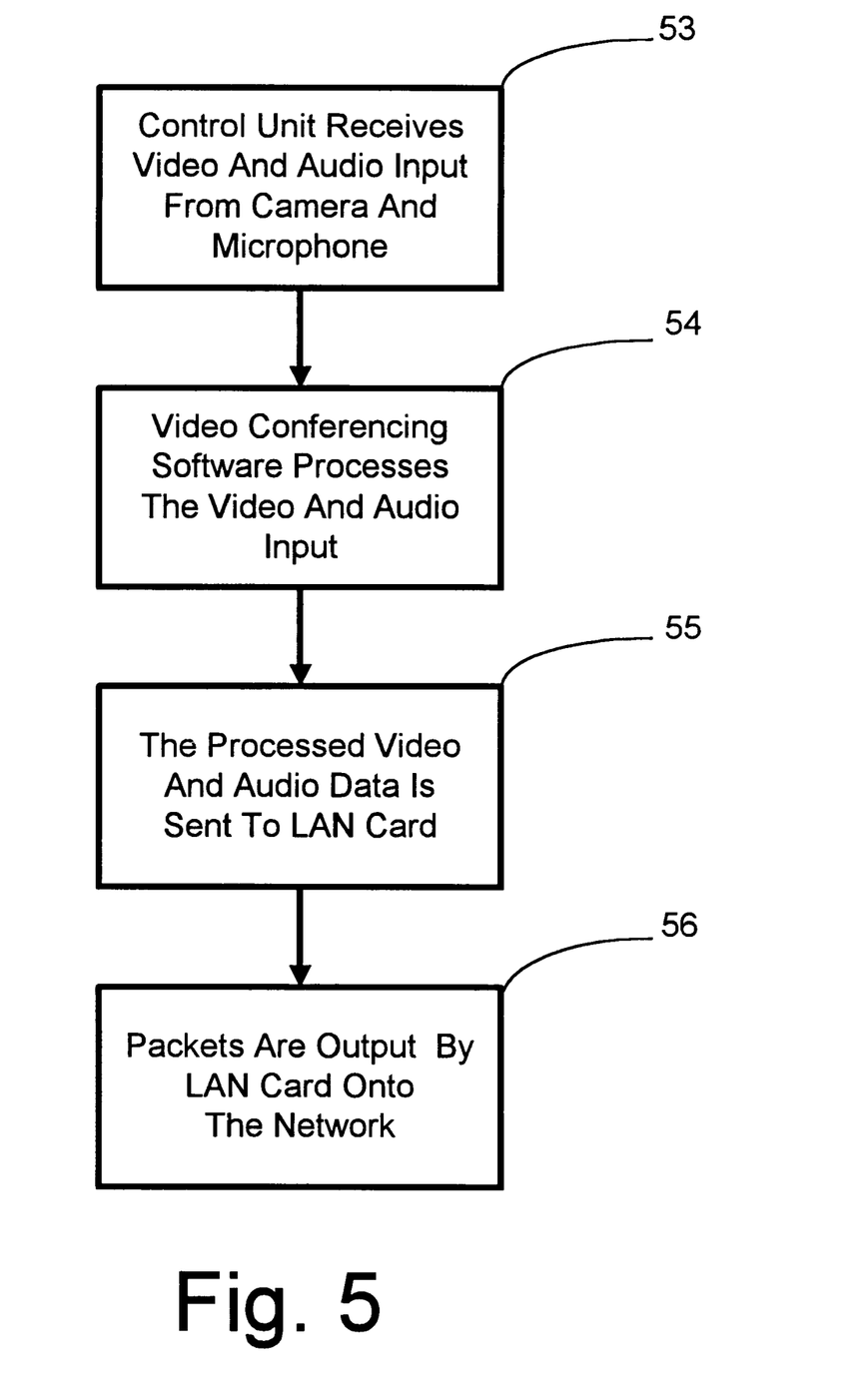
FIG. 5 is a flow chart demonstrating the processing and packeting of video and audio data at the patient monitoring station control unit shown in FIG. 2 before the packets are sent to the central monitoring station shown in FIG. 1.

FIG. 5 is a flow chart functionally illustrating the processing of videoconferencing data received by control unit 22 from videoconferencing equipment 23 via videoconferencing interface device 26. Videoconferencing equipment 23 includes a camera and microphone for obtaining video and audio images of the patient. The videoconferencing software comprised by the videoconferencing interface device 26 processes the video and audio input into a format suitable for the communications device to packet, as indicated by block 54. The data is then provided to the communications device, as indicated by block 55.

As stated above, preferably the communications protocol used with the present invention is TCP/IP. It will be understood by those skilled in the art the manner in which the data is formatted prior to being sent to the communications device to be packeted. Generally, the data is provided to the communications device in a serial bit stream. The identity of the patient and the identity of the central monitoring station to which the data is to be sent is also provided to the communications device. In the case where diagnostic measurement data from one or more of the medical devices is being sent with the videoconferencing data, an indication of the type of measurement being sent and a representation of the measurement itself is also provided to the communications device. Optionally, other types of information may also be provided to the communications device, such as the date and time of the measurement, the type of medical device which took the measurement, and the location or identity of the patient monitoring station.

TCP/IP then parses the data into packets, each packet including a field indicating the destination to which the packet is being sent. The packets are then output by the communications device onto the network, as indicated by block 56. Therefore, at a minimum, the packets sent which correspond to a particular measurement will include an indication of the identity of the patient, the type of measurement being transmitted, and a representation of the measurement itself. The plurality of packet data fields define the identity of the patient, an indication of the type of measurement, and a representation of the measurement itself.

The central monitoring stations 11 are essentially the same as the patient monitoring station, with the exception that the central monitoring stations do not comprise a medical device interface or the medical devices. The processing of data at the central monitoring stations 11 is essentially the same as that depicted in FIGS. 3 and 5 for the patient monitoring stations 18, with the exception that no data for controlling medical devices is received by the central monitoring stations 11. Also, the telemedicine software at the central monitoring stations 11 is different from the telemedicine software at the patient monitoring station. The telemedicine software at the central monitoring station includes one or more routines for analyzing measurement data to determine the type of measurement data received, e.g., whether the data is blood pressure data, temperature data, pulse oximetry data, etc. The telemedicine software at the central monitoring station also includes a functionality for determining the identity of the patient to whom the data corresponds. This can be accomplished by parsing the de-encapsulated data using the order of the data in the de-encapsulated data stream and preselected indications contained in the data stream to determine the measurement type, the measurement itself, and the identity of the patient.

A medical file maintained for the patient at the central monitoring station may then be updated to reflect the received measurement. Alternatively, the medical files may be maintained at a server located outside of the central monitoring stations 11 which is capable of being accessed by the central monitoring stations and/or by the patient monitoring stations 18. It will be apparent to those skilled in the art the manner in which such an analysis is performed.

It will be apparent to those skilled in the art that many variations and modifications can be made to the present invention without departing from the spirit and scope of the present invention. All such variations and modifications are intended to be within the scope of the present invention, as set forth in the following claims.

What is claimed is:

1. A telemedicine system for transmitting voice, video and medical data between a central monitoring station and a patient monitoring station over a network, the telemedicine system comprising:

a first control unit located at the patient monitoring station, the control unit receiving medical data from one or more medical instruments in communication with the control unit and delivering the medical data to a first communication device in communication with the control unit, the communication device encapsulating the medical data in packets in accordance with a preselected communication protocol and outputting the packets onto the network; and a second control unit located at the central monitoring station, the second control unit being in communication with a second communication device, the second communication device receiving the packets output by the first communication device onto the network, the second communication device de-encapsulating the packets to reconstruct the medical data, the reconstructed medical data being provided to the second control unit;

wherein the first control unit receives video and voice data from videoconferencing equipment in communication with the control unit and delivers the video and voice data to the first communication device, the communication device encapsulating the video and voice data in packets in accordance with the preselected communications protocol and outputting the packets onto the network, wherein the second communication device receives the packets encapsulating the video and voice data and de-encapsulates the packets to reconstruct the video and voice data, the second communication device providing the video and voice data to the second control unit.

2. The telemedicine system of claim 1, wherein the telemedicine system is for transmitting voice, video and medical data between a plurality of central monitoring stations and a plurality of patient monitoring stations, each patient monitoring station comprising said first control unit and each of said central monitoring stations comprising said second control unit.

3. The telemedicine system of claim 1, wherein the network is a community access television (CATV) network.

4. The telemedicine system of claim 3, wherein the communications protocol is TCP/IP.

5. The telemedicine system of claim 1, wherein the network is an asynchronous transfer mode (ATM) network.

6. The telemedicine system of claim 5, wherein the communications protocol is TCP/IP.

7. The telemedicine system of claim 1, wherein the network is the Internet.

8. The telemedicine system of claim 7, wherein the communications protocol is TCP/IP.

9. The telemedicine system of claim 1, wherein the network is a Public Switched Telephone Network (PSTN).

10. The telemedicine system of claim 9, wherein the communications protocol is TCP/IP.

11. The telemedicine system of claim 1, wherein the network is an Integrated Services Digital Network (ISDN).

12. The telemedicine system of claim 11, wherein the communications protocol is TCP/IP.

13. The telemedicine system of claim 1, wherein the network is a local area network (LAN).

14. The telemedicine system of claim 13, wherein the communications protocol is TCP/IP.

15. The telemedicine system of claim 1, wherein the network is a wide area network (WAN).

16. The telemedicine system of claim 15, wherein the communications protocol is TCP/IP.

17. The telemedicine system of claim 1, wherein the network is a hybrid network consisting of a combination of one or more networks selected from the group consisting of: a community access television (CATV) network, an asynchronous transfer mode (ATM) network, the Internet, a Public Switched Telephone Network (PSTN), an Integrated Services Digital Network (ISDN), a local area network (LAN), or a wide area network (WAN).

18. The telemedicine system of claim 17, wherein the communications protocol is TCP/IP.

19. A method of acquiring and transporting data in a telemedicine system, the method comprising the steps of:

generating medical device command data and application-level data in a control unit located at a central monitoring station, the data being represented by one or more bits;

encapsulating the data in packets in accordance with a preselected communications protocol, each packet comprising a designation of a patient monitoring station to which the packet is being sent;

outputting the packets onto a network;

receiving the packets at the patient monitoring station designated by the designation comprised in the packets;

de-encapsulating the packets to reconstruct the data;

providing the reconstructed data to a control unit located at the patient monitoring station;

obtaining video and voice data from videoconferencing equipment located at the central monitoring station;

encapsulating the video and voice data in packets in accordance with the preselected communications protocol, each packet comprising the designation of the patient monitoring station;

outputting the packets onto the network;

receiving the packets at the patient monitoring station;

de-encapsulating the packets to reconstruct the video and voice data; and providing the reconstructed video and voice data to the control unit located at the patient monitoring station.

* * * * *